United States Patent [19]

Clague et al.

[11] Patent Number: 5,441,482

[45] Date of Patent: Aug. 15, 1995

[54] JET DRIVEN SURGICAL SUCTION DEVICE AND METHOD OF USING

[75] Inventors: Cynthia T. Clague, Minneapolis; Perry L. Blackshear, Jr., Mahtomedi, both of Minn.

[73] Assignee: The Regents of the University of Minnesota, Minneapolis, Minn.

[21] Appl. No.: 241,284

[22] Filed: May 11, 1994

[51] Int. Cl.$^6$ .................. A61M 1/00; A61M 25/00
[52] U.S. Cl. ......................... 604/35; 604/28; 604/43; 604/45; 604/264; 261/79.2
[58] Field of Search ............ 604/27, 29, 22, 35, 604/118, 119, 149, 4, 5, 6, 902, 93, 266; 239/590.5; 261/DIG. 75, 79.2

[56] References Cited

U.S. PATENT DOCUMENTS

| | | | |
|---|---|---|---|
| 3,912,468 | 10/1975 | Tuschiya et al. | 55/159 |
| 3,952,743 | 4/1976 | Harrison | 128/276 |
| 3,955,573 | 5/1976 | Hansen et al. | 128/276 |
| 4,002,170 | 1/1977 | Hansen et al. | 128/276 |
| 4,170,457 | 10/1979 | Tetro | 55/46 |
| 4,345,919 | 8/1982 | Wilkinson et al. | 55/41 |
| 4,368,118 | 1/1983 | Siposs | 210/136 |
| 4,475,932 | 10/1984 | Hull et al. | 55/170 |
| 4,516,398 | 5/1985 | Wuchinich | 604/22 |
| 4,555,253 | 11/1985 | Hull et al. | 55/170 |

(List continued on next page.)

FOREIGN PATENT DOCUMENTS

| | | | |
|---|---|---|---|
| 0128556 | 12/1984 | European Pat. Off. | B01D 19/00 |
| 0156777 | 10/1985 | European Pat. Off. | B04C 5/12 |
| 0318993 | 6/1989 | European Pat. Off. | A61M 1/36 |

(List continued on next page.)

OTHER PUBLICATIONS

F. S. Cross et al., "A New Type Suction Tip Especially Design for Intreacardiac Surgery", *J. Thoracic Cardiovascular Surg.* 41:3:412–415, Mar. 1961.

(List continued on next page.)

*Primary Examiner*—Randall L. Green
*Assistant Examiner*—Dennis Ruhl
*Attorney, Agent, or Firm*—Joseph F. Breimayer; Grace P. Malilay

[57] ABSTRACT

A probe for use in collecting liquids entrained with a gaseous component, particularly collecting a patient's blood with entrained gas bubbles from a surgical site for autologous reinfusion. The probe separates the gaseous component from the collected liquid, particularly separating air bubbles from blood cells to inhibit hemolysis, platelet degradation and protein denaturation. An elongated probe body has a distal end to be inserted into the liquid to be collected through an inlet by jet pump action into a centrally disposed mixing chamber. A diffuser is formed within the probe body proximal to and in axial alignment with the inlet and mixing chamber leading to a liquid exit. A jet pump nozzle is formed in the probe distal tip surrounding the inlet in the form of an annular chamber into which pressurized drive fluid is introduced through a distribution channel system extending along the probe body from the proximal end. The drive fluid is ejected in a swirling vortex from the jet pump nozzle around the periphery of the mixing chamber effecting a sub-atmospheric pressure for suctioning the liquid to be collected and the gaseous component thereof into the inlet and mixing chamber. The drive fluid mixes therewith in the swirling vortex and propels the mixture into the diffuser while concentrating the gaseous component in the center of the swirling vortex as a stream. A gas evacuation tube is oriented in the centrally disposed concentrated gaseous stream for evacuating the gaseous component from the mixture before it is propelled into the diffuser. In the autologous reinfusion context, the entrained air bubbles are concentrated and removed in the probe from the blood as they are suctioned into the swirling vortex to reduce hemolysis. When mixed in the vortex, the blood and drive fluid mixture is pressurized to inhibit further air bubble formation.

24 Claims, 10 Drawing Sheets

U.S. PATENT DOCUMENTS

| | | | |
|---|---|---|---|
| 4,560,373 | 12/1985 | Sugino et al. | 604/30 |
| 4,698,207 | 10/1987 | Bringham et al. | 422/46 |
| 4,772,256 | 9/1988 | Lane et al. | 604/4 |
| 4,775,360 | 10/1988 | Lane et al. | 604/4 |
| 4,876,066 | 10/1989 | Bringham et al. | 422/46 |
| 4,932,987 | 6/1990 | Molina | 55/159 |
| 4,976,682 | 12/1990 | Lane et al. | 604/4 |
| 5,055,198 | 10/1991 | Shettigar | 210/650 |
| 5,061,236 | 10/1991 | Sutherland et al. | 604/4 |
| 5,098,376 | 3/1992 | Berry et al. | 604/26 |
| 5,149,341 | 9/1992 | Taylor et al. | 55/36 |
| 5,300,022 | 4/1994 | Klapper | 604/266 |

FOREIGN PATENT DOCUMENTS

| | | | |
|---|---|---|---|
| 1506082 | 9/1977 | United Kingdom | A61M 1/00 |
| WO94/03098 | 2/1994 | WIPO | |

OTHER PUBLICATIONS

S. Bostrom et al., "New Microsurgical Suction Tubes", *Acta Neurochirugica*, (1990), 104:156–157.

H. J. ten Duis et al., "Improved Hemocompatibility In Open Heart Surgery", *Trans. ASAIO*, (1978) 656–661.

T. Hirose et al., "Reduction of Perfusion Hemolysis by the Use of Atraumatic Low–Pressure Suction", *J. Thoracic Cardiovascular Surgery*, 47:2:242–247, Feb. 1964.

M. Peskovitz, "A History of Surgical Suction from Dieulafoy to Gomco", *Surg., Gyn. & Obs.*, (Sep. 1989), 169:3:266–274.

G. Spencer et al., "A Non-clogging Suction System", *Clinical Orthopedics*, 128:200–201, Oct. 1977.

L. Tinkler, "A Complete Suction System for Operative Surgery", *Brit. J. Surgery*, 64:653–654, Sep. 1977.

R. Dyer et al., "Atraumatic Aspiration of Whole Blood for Intraoperative Autotransfusion", *Am. J. Surg.*, (May 1972), 123:510–514.

Y. Hosada, "A New Pericardial Sucker: Omni Sucker for Better Aspiration of Interpericardial Blood", *Ann. Thorac. Surg.*, 46:5:582–583, Nov. 1988.

5,441,482

JET DRIVEN SURGICAL SUCTION DEVICE AND METHOD OF USING

FIELD OF THE INVENTION

The present invention relates to methods and apparatus for recovering patient's blood from a surgical or wound site for autologous transfusion and more particularly to an improved suction device or probe usable therewith for separating infused air bubbles from a mixture of blood cells, plasma and washing solutions.

BACKGROUND OF THE INVENTION

Clean, viable blood has become a precious resource in this age of complex invasive surgeries for treatment of disease or injuries while donor blood supplies are becoming both scarcer and suspect in light of potential HIV and hepatitis contamination and transmission via transfusion. Autologous transfusion, the use of a patient's own blood drawn before elective surgery or from the surgical field during the procedure or postoperatively from the wound site, has been endorsed as the safest form of transfusion and has become increasingly more popular. Autologous transfusion is desirable because it eliminates the risks encountered with homologous transfusion of donor blood. The risks of homologous transfusion include disease transmission, transfusion reaction and decreased quality of bank blood stored over time.

Aside from eliminating risks of homologous transfusion, autologous transfusion is desirable because it acts as an immediate blood source for trauma cases, conserves blood bank blood for cases where autologous transfusion is inappropriate and provides an option for patients with religious convictions prohibiting use of donor blood. For trauma cases involving rapid bleeding, autotransfusion can prevent death by providing an immediate, large source of blood that doesn't need to be cross-matched. In cases of rapid, profuse bleeding, available banked blood may be depleted or the blood cannot be given fast enough.

Intraoperative autotransfusion is the recovery of the patient's blood lost during surgery and reinfusion of that blood at a later time during the procedure. The reinfusion can be direct or after processing of the blood performed in the operating room or a central facility. During bypass surgery, for example, blood returning to the right heart is removed by suction (referred to as cardiotomy) and returned to the blood circuit after processing to remove bubbles, debris and the like. In other procedures, the blood pooling at the operative site is removed by suction.

Postoperative autotransfusion is the salvaging of blood following surgery. Blood draining into the chest, for example, following surgery or trauma must be removed by a drainage or aspirating system to prevent its accumulation. Such blood is suited to salvage and reinfusion because it is usually defibrinated, sterile and does not need to be anticoagulated or washed prior to reinfusion.

FIG. 1 depicts in simplified form a system for collecting, without washing, and processing pooled blood at a patient's operative or postoperative surgical site 10 to reinfuse the blood in an autologous transfusion. Basically, blood is collected into a reservoir 12 (or directly into a reinfusion bag), through suction applied through surgical tubing 14 either by wall vacuum or by a roller pump, and filtered and reinfused. In one system as depicted in FIG. 1, blood is collected into a disposable liner bag 16 within a reusable rigid canister 18 forming the reservoir 12. The liner bag 16 has a filter 20, and the interior of the rigid canister 18 is connected to a wall vacuum source or roller pump through surgical tubing. Blood from the liner bag 16 is either drained by gravity into a transfer pack or is directly infused through an infusion catheter 22 (optionally using a roller pump) through the filter 21 back into the patient as depicted in the dotted line position of the liner bag 16 and filter 21.

Turning to the collection of the blood from the surgical site 10, the vacuum drawn through the surgical tubing causes suction to occur in the liner bag 16 to draw blood through flexible surgical tubing 26 extending to the attached suction tube or probe 30. Suction tubes or probes 30 come in many configurations, but basically are straight or curved, elongated tubular instruments having a fitting at one end for attachment to the surgical tubing 26 and an open tip end that may be submerged in the pooled blood at the site 10. A vacuum is drawn through the medical tubing 26 to suction the blood, debris and body fluids into the tip and convey it to the reservoir 12. Tip configurations vary, but efforts have been made incorporating end shields and/or side openings to inhibit closure of the opening on contact of the end with tissue and filters to filter out and inhibit obstruction of the openings by floating debris. Typically, the entire probe 30 is autoclavable for reuse, and the tips are removable for cleaning. Simple suction tubes are also referred to as aspirators and are used in other contexts to remove surgical debris during operative procedures or accumulated fluids and gases from closed surgical sites.

Anticoagulant from a container 24 is added either at the suction tip or is added to the collected blood before it is reinfused. In the example of FIG. 1, the anticoagulant is infused from anticoagulant container 24 through medical tubing 28 into the probe 30 and mixed with the blood being suctioned out in a manner suggested in U.S. Pat. No. 3,955,573, for example. The mixture may take place at the tip of or at the widened section near the attachment end with the tubing 26 and 28. Thorough mixing of the anticoagulant with the aspirated blood at the probe tip is advocated, and examples of tip configurations for effecting a vortex mixture of the blood and anticoagulant suctioned in by the vacuum drawn through the suction tube are depicted, in the '573 patent.

Infusing unwashed blood can mean infusion of high levels of free hemoglobin, debris from the surgical field and "procoagulants". The blood infused may also contain added anticoagulant as described above and irrigating solutions that may be used during the procedure to wash the surgical site 10. A wash fluid, e.g. a mixture of saline and anticoagulant, may also be introduced at the tip of the suction probe to wash the orifice and to add the anticoagulant as disclosed, for example, in U.S. Pat. No. 4,976,682, described below.

In a further U.S. Pat. No. 3,952,743, a probe used to remove tissue, e.g. brain tumor cells, has a coaxial tubular arrangement, and a wash fluid is introduced down and diverted in the outer tube to effect a vortex as it passes out of the outer tube at the tip to aid in removing any tissue caught at the orifice to the inner suction tube. The vacuum suction applied to the inner tube to suction the tissue also suctions the wash fluid directed to the probe tip. Thus, in different contexts, it is known to introduce a wash fluid with or without anticoagulant, to the tip of a suction probe or aspirator.

FIG. 2 depicts a system for washing the blood after it is collected which includes the additional apparatus and steps of adding and removing the wash fluid downstream from the probe 30, including the wash fluid container 40, reinfusion blood bag 42, reversible pump 44, centrifuge 46 and connecting surgical tubes 38, 48, 50, 52, 54. Valves 53, 55 and 57 are also included in tubes 38, 48, and 50, respectively to be opened or closed during these additional steps. The most widely studied and reported device for concentrating and washing red blood cells from salvaged blood is the Haemonetics Cell Saver system generally depicted in FIG. 2.

With the system of FIG. 2, blood is collected from the operating site using a double-lumen suction probe 30 which allows diluted anticoagulant to be mixed with blood as it is being aspirated. The mixed blood and anticoagulant solution (and any wash fluid in the operating site 10) is passed through a 180 micron macrofilter (not shown) to remove gross debris and is initially collected into a standard cardiotomy reservoir 12. When there is enough blood for processing, the mixed blood and anticoagulant solution is routed from the reservoir 12 into a centrifuge bowl 46 by opening valve 53 and operating reversible pump 44 in a first direction. Valve 53 is then closed and valve 55 is opened. In the centrifuge bowl, the blood is washed with an isotonic saline fluid, pumped from container 40 through the open valve 55, and concentrated. The supernatant layer containing white blood cells, platelets, plasma fractions, heparin, free hemoglobin, saline fluid and other cellular debris is generally discarded through the tubing 54. Then, the valve 55 is closed, and valve 57 is opened. The pump direction is reversed to pump the packed red blood cells into the infusion bag 42 and returned to the patient through tubing containing a 20 micron filter (not shown).

Many concerns exist or have existed regarding the reinfusion of salvaged blood (with or without the extra processing of FIG. 2), some real and some theoretical. The primary concerns are formation of microemboli and air emboli, disruption of normal coagulation, dissemination of infection or malignancy and hemolysis. Microemboli such as platelet aggregates can be removed by filtering blood through a 40 micron micropore filter prior to reinfusion to the patient. Concerns about air entrapment and resulting air emboli occurring during the processing and infusion of the blood have diminished with the incorporation of fail-safe air separation devices added to newer systems, and air embolization is unlikely with the new techniques and careful attention. Newer systems and the washing of salvaged blood have also nearly eliminated reports of coagulopathy. Dissemination of infection or malignancies have only infrequently been reported. The thrombocytopenia and minor coagulation disorders occurring after patients have had massive amounts of blood autotransfused are generally related to massive blood replacement and multiple injuries rather than to intraoperative autotransfusion per se.

Following salvage and processing, the number and proportion of cellular components are altered, some cells have decreased function and plasma components are missing, but red blood cell survival, resistance to lysis and function is normal. White cell counts range from 6600 to 17000 per microliter and the cells are severely damaged. Mean platelet counts have been found to be 16000 to 67000 per microliter, and the platelets are likely to have decreased function or no function because of mechanical damage during filtering and suctioning. Potassium levels are low (1.5 mmol/l), proteins are lost, and the product is devoid of coagulation factors. The washing also removes undesirable parts of the unwashed blood such as free hemoglobin and myoglobin from the plasma as well as cellular debris, particles of bone, activated clotting factors and activated platelets. Intact red blood cells following salvage, centrifuging and washing have normal survival, resistance to osmotic lysis and function. The red blood cells have normal to increased levels of 2,3 DPG but are potassium depleted. Typical hematocrit levels are 50-60%.

Hemolysis is a genuine concern. The suctioning of blood that occurs with autologous transfusion has been found to be harmful to the blood, particularly to platelets, red blood cells and elements of the immune system. This damage is believed to be caused by the suction of air bubbles with the blood components which causes hemolysis, clot formation or "drying" of the blood as noted in the above-referenced '682 patent and elsewhere. The high level of free hemoglobin encountered with vacuum suctioning of blood (and not removed by centrifuge) has been associated with acute cases of renal dysfunction and failure. Excessive vacuum levels leads to blood cell damage due to turbulent sheer stress and causes suctioning of air mixed with the blood and is a major cause of hemolysis as the air bubbles mix with and contact blood cells. The resulting red blood cell damage also diminishes the amount of packed red blood cells that can be recovered and returned to the patient during autologous transfusion.

Cardiotomy suction is indicated as a primary factor in the hemolysis that occurs with cardiopulmonary bypass operations. It has been reported that during a half-hour of perfusion, hemolysis was not detected, but at the initiation of intracardiac suction, hemolysis started to rise and showed a steady increase in plasma hemoglobin with continuous suctioning. The hemolysis in the general circuit remained low until the suctioned blood was added to the circuit. Other studies showed that plasma hemoglobin levels jumped and increased rapidly with the start of cardiotomy suction. Following cardiopulmonary bypass in human patients, plasma hemoglobin in the radial artery averaged 41 mg/dl but in the cardiotomy reservoir blood averaged 384 mg/dl.

The above-referenced '682 patent discloses a recognition of these problems and attempts to reduce the contact of air bubbles with blood, and the resulting hemolysis, during suction. The probe is provided that attempts to avoid the suction of air by supplying an anticoagulated wash fluid forming a "dynamic droplet" at the probe tip inside a porous shield. As a vacuum is applied, blood passing through the porous shield and the wash fluid are drawn in by suction, purportedly minimizing the suction of air, should the site become dry of blood. A system is provided, including an air bubble detector in the suction probe, for regulating the suction in proportion to the bleeding rate at the wound site and the quantity of bubbles detected in the solution passing through the probe. As bubbles are detected, the suction rate is increased or decreased in an effort to reduce the bubble concentration.

Problems to be Solved by the Invention

Although it is proposed in the '682 patent to reduce the possibility of suctioning air bubbles with the blood and fluid wash solution, it is stated therein that those nevertheless entrained with the solution present are drawn all the way through the tubing and into the reservoir as in the conventional suction probes. The air bubbles rise to the surface of the blood and fluid wash, and the air escapes over time. The difficulty with such an approach is that the exposure of blood cells to the air bubbles that are present is sufficiently long to effect hemolysis and reduce the quantity of viable blood cells for reinfusion.

In other material handling contexts, particularly in other medical applications, a need exists for a suction device for drawing in materials, e.g. tissue samples, cell cultures and other fluids, and separating high and low density components within the probe.

SUMMARY OF THE INVENTION

It is therefore an object of the present invention to reduce contact between blood cells and air bubbles drawn into a suction probe to reduce significant contact and interaction leading to hemolysis.

It is a further object of the invention to separate blood cells and air bubbles upon their being drawn into a suction probe and to remove a significant volume of the air bubbles from the suction probe before the blood and wash solution is conveyed to the blood processing system employed for autologous transfusion.

It is still another object of the invention to induce a low sub-atmospheric pressure suction in the device sufficient to draw in blood and any air bubbles entrained therein, to separate the drawn in air bubbles from the blood and to subject the drawn in blood and air bubbles to a positive pressure sufficient to increase blood gas saturation levels and inhibit further air bubble formation as the blood is transported through the device.

In a more general aspect, it is a still further object of the present invention to suction other materials into a suction device employing a drive fluid for inducing a low suction pressure sufficient to draw the materials into contact with the drive fluid and then subjecting the drawn in materials to a higher pressure while conveying the materials through the device while separating heavier (high density) and lighter (low density) components of the material to allow their separate withdrawal from the device.

These and other objects of the invention are realized in a suction device for medical purposes for suctioning materials having heavier and lighter components comprising an elongated tubular member having a mixing chamber formed therein having a central axis, a tubular side wall and proximal and distal end openings, an evacuation tube disposed axially within the mixing chamber aligned with the central axis, an inlet formed in communication with the distal end opening for introducing the material to be suctioned into the mixing chamber axially along the center axis, and means for injecting a drive fluid at the distal end opening of the mixing chamber in a swirling vortex flow around the inlet and the side wall for inducing a suction pressure to draw the material through the inlet into the mixing chamber, the swirling vortex flow effecting the mixture of the heavier components of the material with the drive fluid and ejection of the mixture through the proximal end opening while concentrating the lighter components axially to be evacuated through the evacuation tube.

The suction device is preferably coupled with a source of pressurized drive fluid and operated in a system to perform a method of suction and separation of the material into the lighter and heavier components and directing the heavier components to a collection site for processing.

In a specific embodiment, the suction device is a jet pump probe for drawing blood from a patient and mixing the blood and a jet pump drive fluid into a mixture in a mixing chamber as the drive fluid is introduced in the swirling vortex flow at the jet pump nozzle exit plane and for separating entrained air bubbles into a concentrated stream for collection and removal from the mixture, and is employed in a system for collection of blood from a patient for reinfusion further comprising a blood collection reservoir having a blood and drive fluid mixture inlet for receiving blood and drive fluid collected from the patient and separated in the probe from the air bubbles, and a pressurized source of drive fluid coupled to the jet pump nozzle exit plane.

Advantageous Effects of the Invention

The swirling (tangential velocity) component of the jets of drive fluid entering the mixing chamber advantageously creates the vortical flow. The jets induce a low pressure at the inlet to the probe sufficient to draw in the mixed blood and air bubble solution (or other materials). The vortical flow generates a pressure gradient over the flow cross-section which tends to direct entrained air bubbles into the center of the mixing chamber while mixing blood components with the introduced drive fluid. By concentrating the air bubbles into the center of the flow while diluting the blood and concentrating higher density blood cells around the periphery of the mixing chamber, the chance of air bubbles contacting red blood cells is diminished. The vortical flow propels the higher density red blood cells towards the periphery of the mixing chamber while air bubbles will coalesce or clump in the center, thus limiting the surface area available to interact with the red blood cells.

In addition, by collecting the air bubbles in the center of the flow, they can be more easily evacuated from the probe. This evacuation eliminates their interaction with red blood cells during passage through the medical tubing to the blood collection reservoir.

The jet pump probe of the present invention has no moving mechanical parts to exert shear forces on the blood cells and operates above cavitation inducing pressures while generating shear stresses below the hemolytic threshold. The flow rate of the drive fluid governing the suction pressure applied to the drawn in blood or other material does not need to be monitored and regulated as a function of detected air bubble concentrations, since the entrained air bubbles are removed in the probe. The jet pump pressurization of the blood and drive fluid mixture propelled through the probe and attached conduit inhibits formation of air bubbles therein.

BRIEF DESCRIPTION OF THE DRAWINGS

The above and other objects and features of the invention will become apparent from the following detailed description taken in conjunction with the preferred embodiments thereof with reference to the accompanying drawings, which illustrate, by way of example, the principles of the invention, in which like parts are designated by like numerals throughout the views of the drawings and wherein.

DETAILED DESCRIPTION OF THE PREFERRED EMBODIMENT

Figure 1:
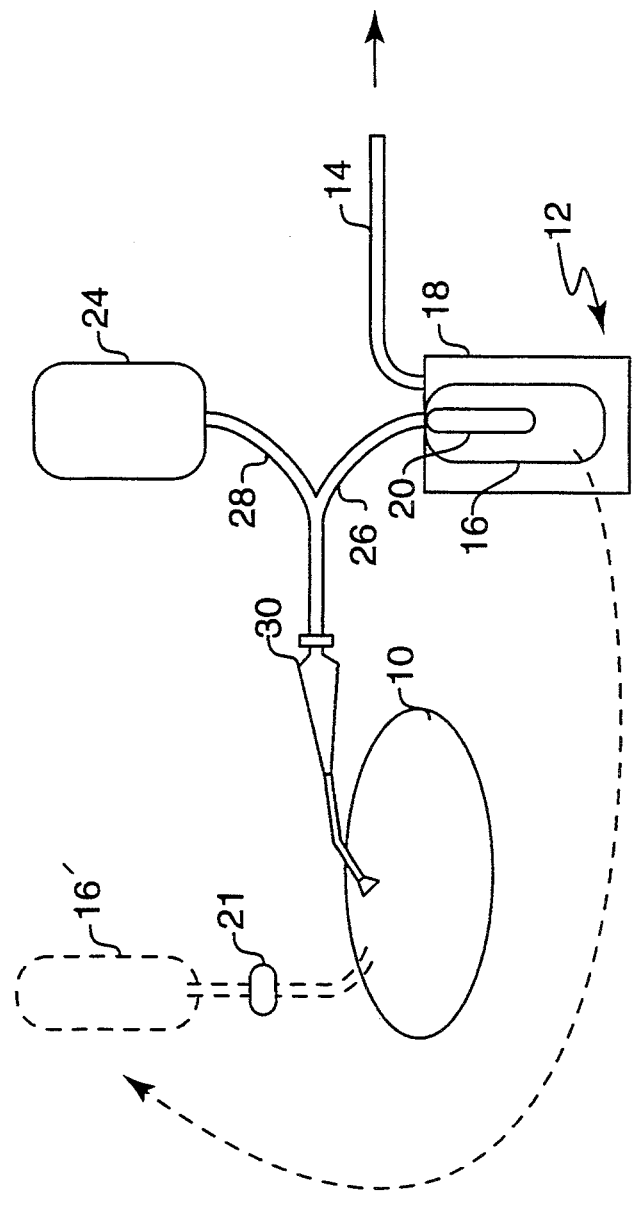
FIG. 1 is a schematic, simplified illustration of an intraoperative autotransfusion system of the prior art without blood washing.
Figure 2:
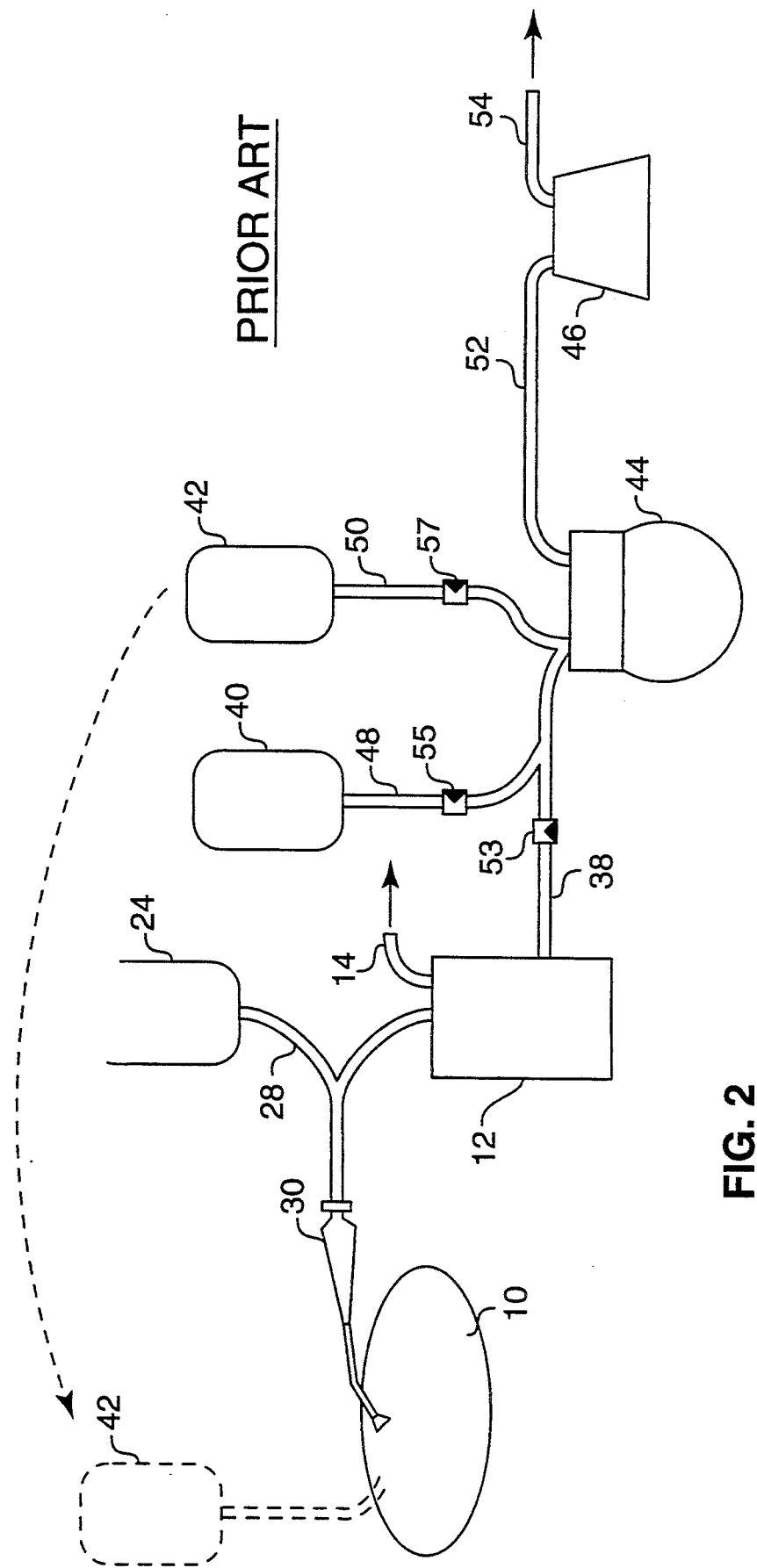
FIG. 2 is a schematic, simplified illustration of an intraoperative autotransfusion system of the prior art with blood washing prior to reinfusion in which the present invention may be implemented.

The air bubbles that appear in a suction apparatus may occur in three ways: entrainment, heterogeneous nucleation or cavitation. Air may become entrained at the suction tip, and the turbulent fluid motion churns the air into boluses and bubbles which are carried along with the blood. Both heterogeneous nucleation and cavitation require nucleation sites from which a bubble can grow. These nucleation sites are generally believed to be microscopic pockets of air trapped in crevices or irregularities on wall surfaces or suspended particles. The crevice or irregularity stabilizes the gas pocket, and gas-filled and vapor bubbles form by diffusion and evaporation into these pockets. Depending upon the conditions in the liquid, the bubbles may grow, dissolve or be stabilized. Above a certain gas nuclei threshold size, the nuclei will grow. If the nuclei is below the threshold size for the current conditions, it will not grow. The cause of cavitation can be hydrodynamic, thermal or acoustic. A hydrodynamic cause of cavitation is the most likely cause in the conventional or jet pump suction device. The cavitation can be transient (short time scale), also called incipient, stable (long time scale) or one type can lead to the other. Hydrodynamic cavitation is believed to spontaneously occur when the pressure in the flow drops below the gas vapor pressure. The exact point at which cavitation actually occurs depends upon the gas content of the liquid and the number and size of the nuclei present.

Three main theories for hemolysis by air bubbles have been described in the literature; bubble collapse, shear stress and contact. The collapse of bubbles in cavitation can generate peak pressures in the range of $10^4$–10 psi which could certainly damage cells. Plus, asymmetric bubble collapse can create jets which could puncture cell membranes. Air bubbles can cause the lysis of red blood cells by shear stress either by turbulent stresses or by the stresses generated as the bubble moves through the blood. In a study of bubble oxygenators, it was found that the tests of an oxygenator which had more marked turbulent movement of foamy (bubbly) blood had a greater rate of hemolysis than the tests where the blood moved more smoothly through the oxygenating column. It has been surmised that the rate of hemolysis is proportional to the velocity of movement of the gas and that greater hemolysis to greater turbulence. It has been observed in a study of cardiotomy suction the rate of hemolysis is proportional to turbulent shear stresses. The blood and air has been observed to move down the suction tubing in short boluses, and that the pressure drop along the cannula was greater than that predicted for laminar flow. In addition, the pressure drop of the blood-air mix had a parabolic relation to flow rate instead of a linear one as would be expected for laminar flow. Individual bubbles moving at high speed could develop near them shear stresses sufficient to damage the red blood cells.

Contact lysis of red blood cells may occur either by a violent collision between a bubble and a cell or by contact between the bubble surface and the cell membrane. A bubble shooting through blood may lyse a cell by the mechanical force generated when the bubble hits the cell. From experimental measurements of the number of intact cells remaining versus exposure time to ultrasound and predictions of the rate of cell-bubble interactions from which the number of intact cells remaining as a function of time could be figured, others have shown that a single interaction is more likely than not to lyse a cell. Another theory of contact lysis is that when the surface of an air bubble contacts the membrane of a cell the surface tension of the air bubble exceeds the membrane strength of the cell, and the cell is lysed.

One aspect of our invention involves the recognition that the blood cells and air bubbles drawn in during suction of the operative or postoperative wound site should be separated as soon as possible to minimize such contact lysis and other causative processes of hemolysis in order to maximize the amount of blood cells available for reinfusion. Our preferred realization of the inventive concept is in a suction probe employing a drive fluid, e.g. saline with or without anticoagulant, jet injected under pressure as a propulsion fluid for blood drawn into the tip orifice of a probe tip, the probe configured as a jet pump operating to separate and concentrate air bubbles drawn in with the blood in a bubble stream that may be separately evacuated from the probe before significant contact with blood cells can occur. The jet pump of the probe configuration is particularly operable as a swirling, annular, parietal jet pump, so that the blood and air bubbles drawn in the tip orifice are separated on entry with the air bubbles centrally entrained in a vortex amenable to immediate evacuation though an axial evacuation tube.

While we at times refer to the device as a suction probe, it will be understood that instead of relying on the wall vacuum or roller pump applying suction to draw the blood into the probe, the drive fluid jet pump creates a relatively low sub-atmospheric pressure at the jet nozzle exit plane sufficient to lift blood from the surgical site to the jet exit at rapid rate. The blood is momentarily exposed to the sub-atmospheric pressure but then entrained by and mixed with the higher velocity fluid jet at a positive pressure that exceeds the gas saturation pressure, inhibiting the release of air bubbles, in a mixing chamber. Momentum is exchanged between the swirling fluid and the lifted blood throughout the mixing chamber. The kinetic energy of the mixture is converted to pressure energy by a diffuser located at the exit of the mixing chamber. The pressure at the diffuser exit is sufficient to drive the mixture out of the suction probe and into surgical tubing to be routed to appropriate processing.

Figure 3:
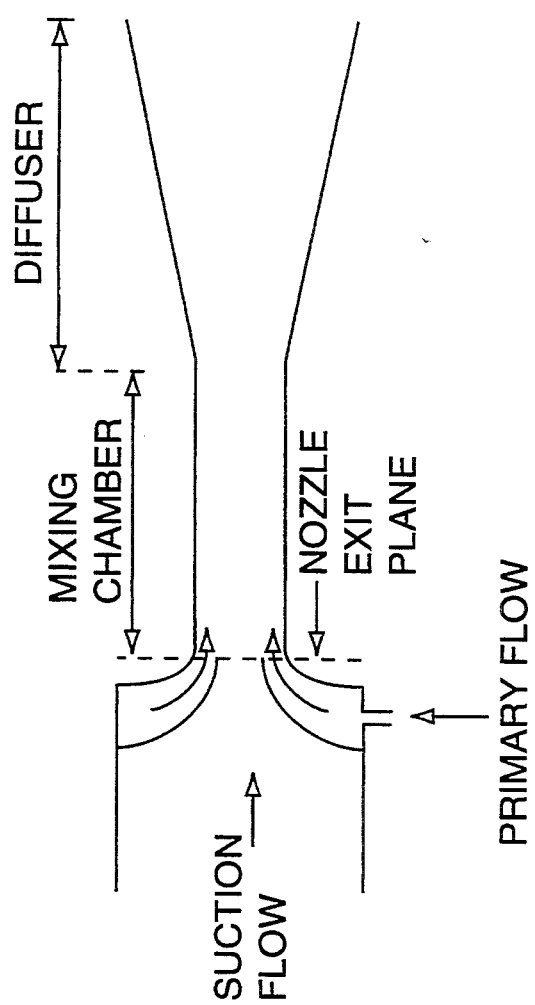
FIG. 3 is schematic view illustrating annular parietal jet pump principles applied in the suction probe of the invention.

FIG. 3 is a schematic view illustrating annular parietal jet pump principles applied in the inventive suction probe. The working basis of a jet pump is the transfer of energy from a high velocity jet to a fluid of lower velocity to effect suction flow. The high velocity jet is created by the conversion of pressure energy into kinetic energy by passage of the pressurized primary flow fluid through an annular driving nozzle. The transfer of energy between the jet and the lower velocity fluid is accomplished in three ways. First, the drop in pressure of the driving jet upon exit from the annular nozzle induces suction flow of the lower velocity fluid in the direction of primary flow. Secondly, the lower velocity fluid is entrained by viscous friction on the periphery of the high velocity jet. Thirdly, the particles in the lower velocity fluid are accelerated by impact with the particles of the higher velocity fluid. Following the mixing of the two fluids in the mixing chamber, the kinetic energy of the mixture is converted to pressure energy by passage through a diffuser. The mixing chamber typically is tubular and has a constant cross-section. The diffuser is conical and expands in cross-section area, and kinetic energy is converted to pressure energy by the configuration of the mixing chamber and diffuser. Flow rate and pressure conditions at the exit of the diffuser are prescribed by the pump's specific application.

The jet pump configuration employed in the preferred embodiment of the invention illustrated in FIGS. 4-10 operates with annular parietal injection. An annular jet is created by forcing the pressurized drive fluid, in this case any biocompatible diluent, e.g. saline or a saline-anticoagulant mixture, between two concentric, tip cones that terminate at a nozzle exit plane at the mixing chamber entrance. The drive fluid is pumped by a pump through channels on the exterior of the mixing throat into the tip of the suction probe and exits between the two cones into the mixing throat. A swirling velocity fluid flow is produced by introducing the drive fluid tangentially at the base of the cones so that the fluid exits the nozzle in a vortex. The interior of the tip of the suction probe serves as the inlet for the blood being suctioned and is rounded at the entrance to minimize blood damage. The blood is pulled into the mixing chamber by the pressure difference between the pool of blood in the surgical site and pressure at the nozzle exit plane. In the mixing chamber the blood and fluid mix and are propelled by the pressure head through the diffuser and into the blood processing system.

The reduction in contact between air bubbles and red blood cells drawn in by the suction flow is accomplished by separating the air bubbles from the main liquid flow in the mixing chamber. The fluid jet at the nozzle exit plane (the entrance to the mixing chamber) having the predominant axial velocity component as well as a tangential velocity component generates the vortical swirl or vortex in the flow. The vortex V shown schematically in FIG. 3 sets up a decreasing pressure gradient from the tubular wall to the center axis of the mixing chamber. This pressure gradient drives a large fraction of the air bubbles into the central, axial region of the mixing chamber where they may be removed from the flow by an axially disposed, small diameter evacuation pipette or tube as described below.

Figure 4:
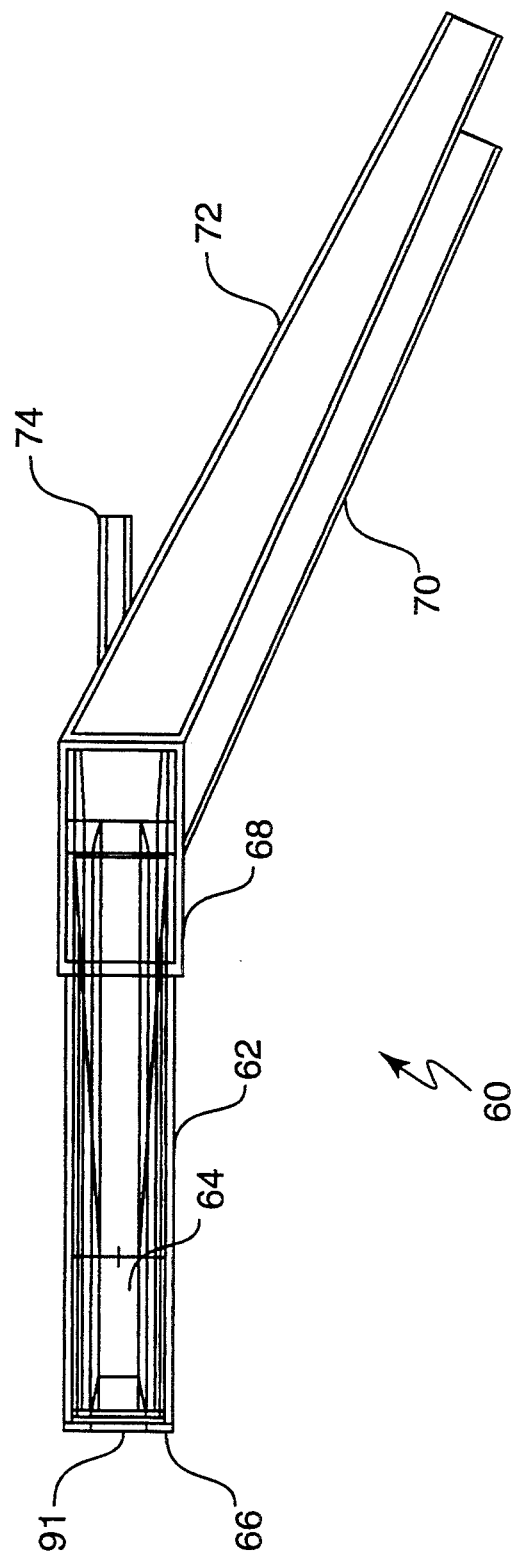
FIG. 4 is a plan view of the suction probe of the present invention.
Figure 5:
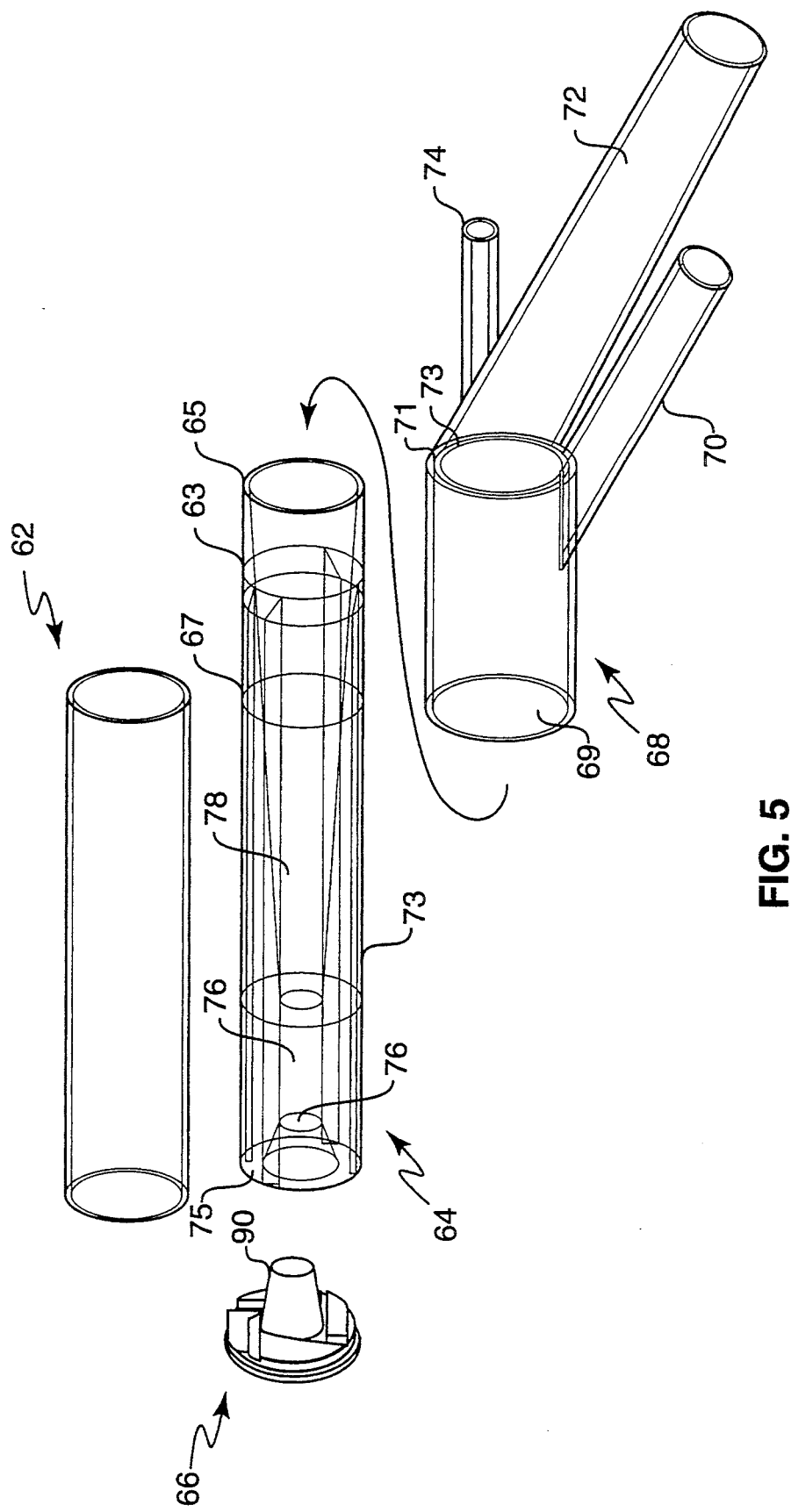
FIG. 5 is a perspective view of the separated components of the suction probe assembled together in FIG. 4.
Figure 6:
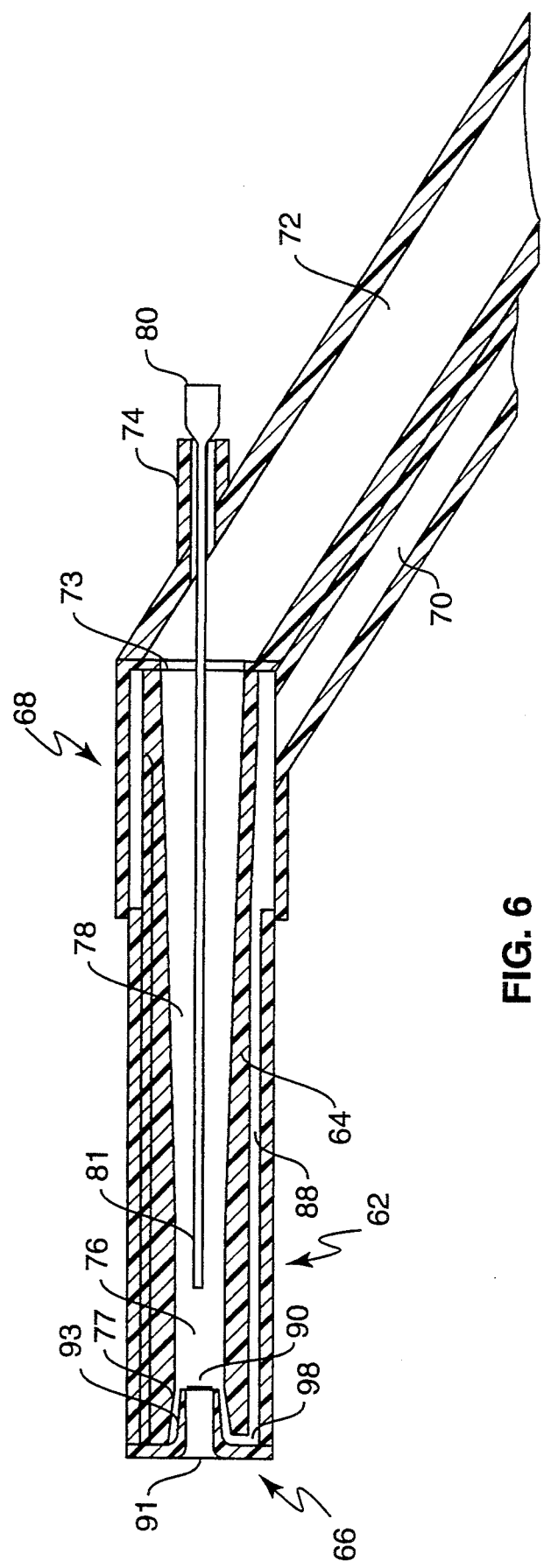
FIG. 6 is a side section view of the suction probe of FIG. 4.

Turning now to FIGS. 4-6, they depict views of a first preferred embodiment of the inventive jet pump probe 60 in assembled and disassembled views of the components thereof, including outer sleeve 62, inner core 64, tip 66 and manifold 68. Tubular sleeve 62 fits snugly around inner core 64 through most of its length from the distal end surface 75 proximally to plane 67. Tip 66 fits against the distal end of the fitted together sleeve 62 and distal end surface 75 as described below. The manifold 68 is tubular, having a fixed diameter and an open end 69 fitting tightly over a short segment of the proximal end of sleeve 62 just distal to plane 67 and a proximal end 71 having an annular seat formed interiorly. The proximal end 65 of inner core 64 fits inside manifold 68 and abuts the annular seat 73 of proximal end 71, so that a fluid manifold space surrounding the proximal portion of inner core 64 is created as shown in FIG. 6.

Manifold 68 also includes fluid supply tube 70 and blood and drive fluid mixture exit tube 72 both extending angularly to the major axis of manifold 68 and axially extending air bubble evacuation tube 74. Fluid supply tube 70 fits into an opening in the side wall of manifold 68. The mixture exit tube is sealed to the proximal end 71 of manifold 68 and includes the tubular air bubble evacuation tube 74. Air bubble evacuation tube 74 is aligned to the major axis of the assembly and is sized to receive the air evacuation pipette 80 shown inserted in FIG. 6. The angular orientation of the fluid supply and exit tubes 70 and 72 is selectable for handling and visualizing convenience and is not critical to the jet pump operation.

FIG. 6 also shows the constant diameter mixing chamber 76 and the conical diffuser 78 formed within the inner core 64, and the axial alignment of the opening of end 81 to receive air bubbles concentrated centrally by the vortical flow within the mixing chamber 76.

The inlet 91 to the mixing chamber 76 is formed in the tip 66 axially aligned with the axis of the mixing chamber 76 and diffuser 78. The inlet 91 is tapered inward to reduce sharp edges and is formed within the jet cone 90 projecting inward from the tip 66 as shown in FIG. 6. The parietal jet pump action described above effecting vortical flow in the mixing chamber 76 is created by the swirling jet of fluid entering the mixing chamber 76 through a nozzle defined by the conical, distal inner wall 77 of the chamber 76 and the inwardly tapered exterior surface 93 of hollow jet cone 90 that extends axially from tip 66. As a result of the low, sub-atmospheric pressure created by the drive fluid pumped through the nozzle as described above with respect to FIG. 3, the blood is drawn in through the tapered inlet 91 and traverses it very rapidly. The blood mixes in the mixing chamber 76 with the drive fluid injected through the nozzle in a swirling vortex that concentrates the lighter air bubbles axially and into the open end 81 of the pipette 80 to be drawn away. The blood and drive fluid mixture exits through the diffuser 78 and the exit tube 72.

Figure 7:
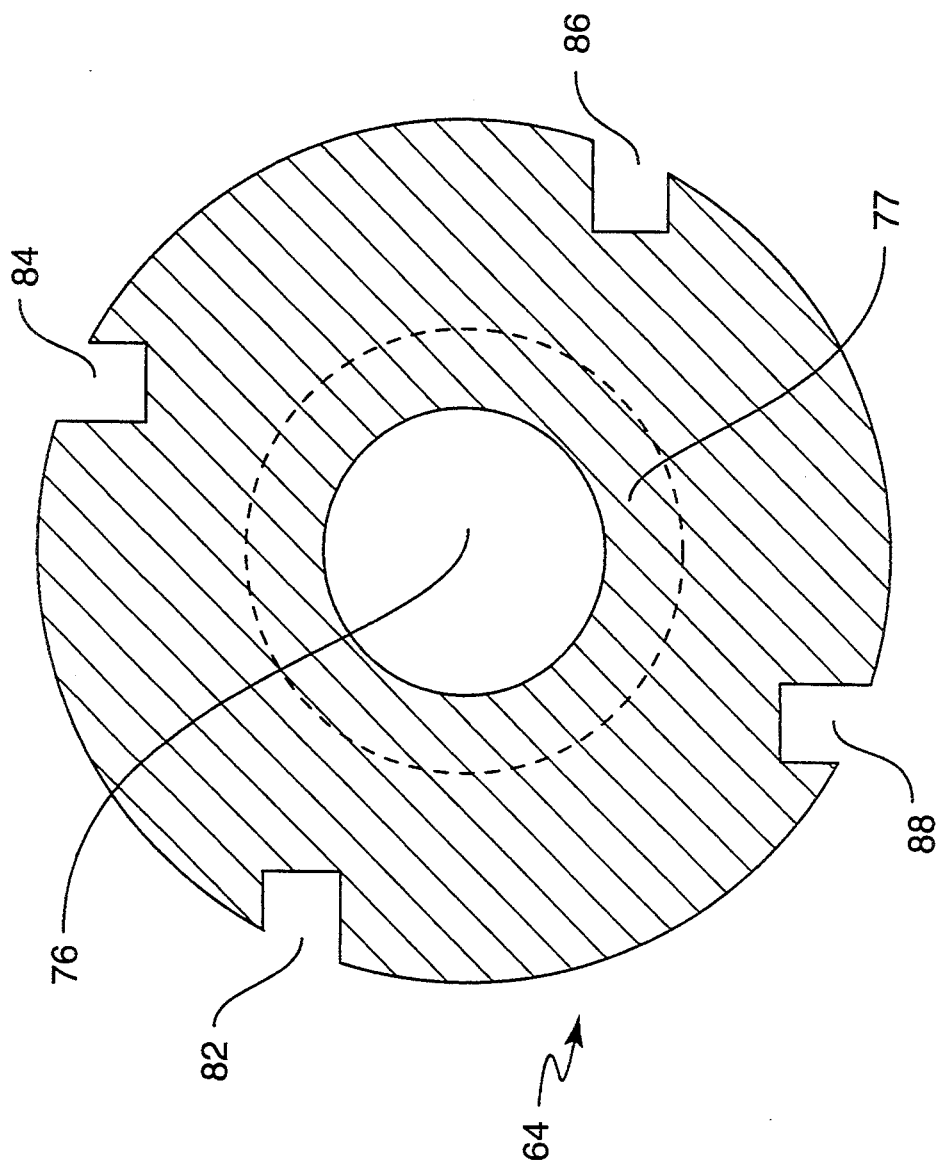
FIG. 7 is a tip end view of the inner core of the suction probe of FIG. 4.

Turning to the manner in which the fluid is introduced into the nozzle, the inner core 64 is formed with four, spaced apart, axial fluid supply channels 82, 84, 86, 88 extending from the distal end face 75 nearly to points near the proximal end 65 where they terminate in a band region 63 shown in FIG. 5 which is within the manifold chamber when the components are assembled. FIG. 7 is a cross-section view taken at the section 59 (viewed from the proximal side) of inner core 64 in FIG. 5. FIG.

7 shows that the axial fluid channels 82, 84, 86, 88 are cut into the outer circumference of inner core 64 and aligned tangentially of the cylindrical wall of the central, circular mixing chamber 76. Axial fluid channel 88 is shown in cross-section in FIG. 6 extending from within the chamber of manifold 68 to the distal end face 75 where it is in communication with the tangential fluid channel 98 tangentially bearing alongside the cone 90.

Figure 8:
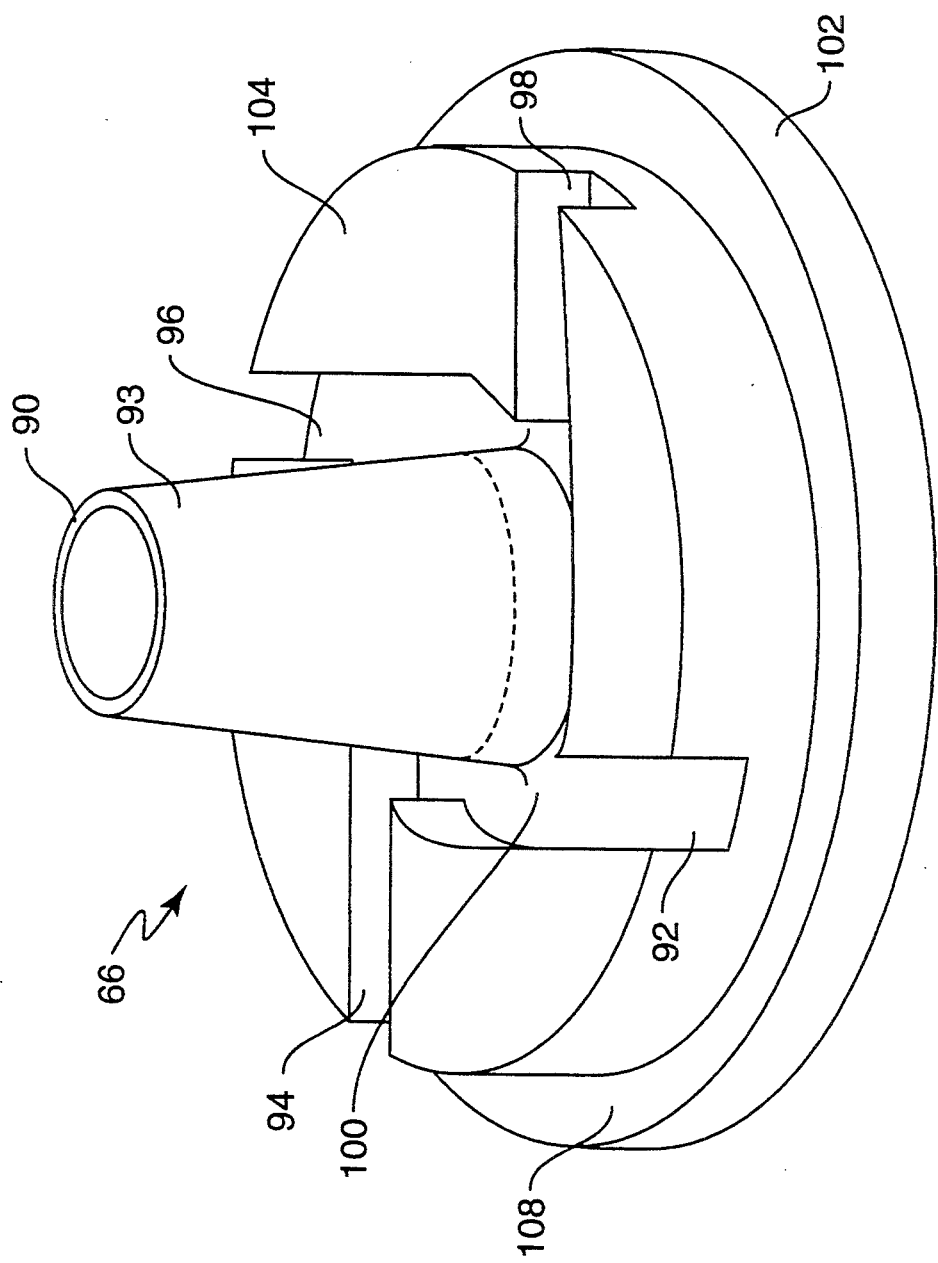
FIG. 8 is a perspective view of the tip of the suction probe of FIG. 4.
Figure 9:
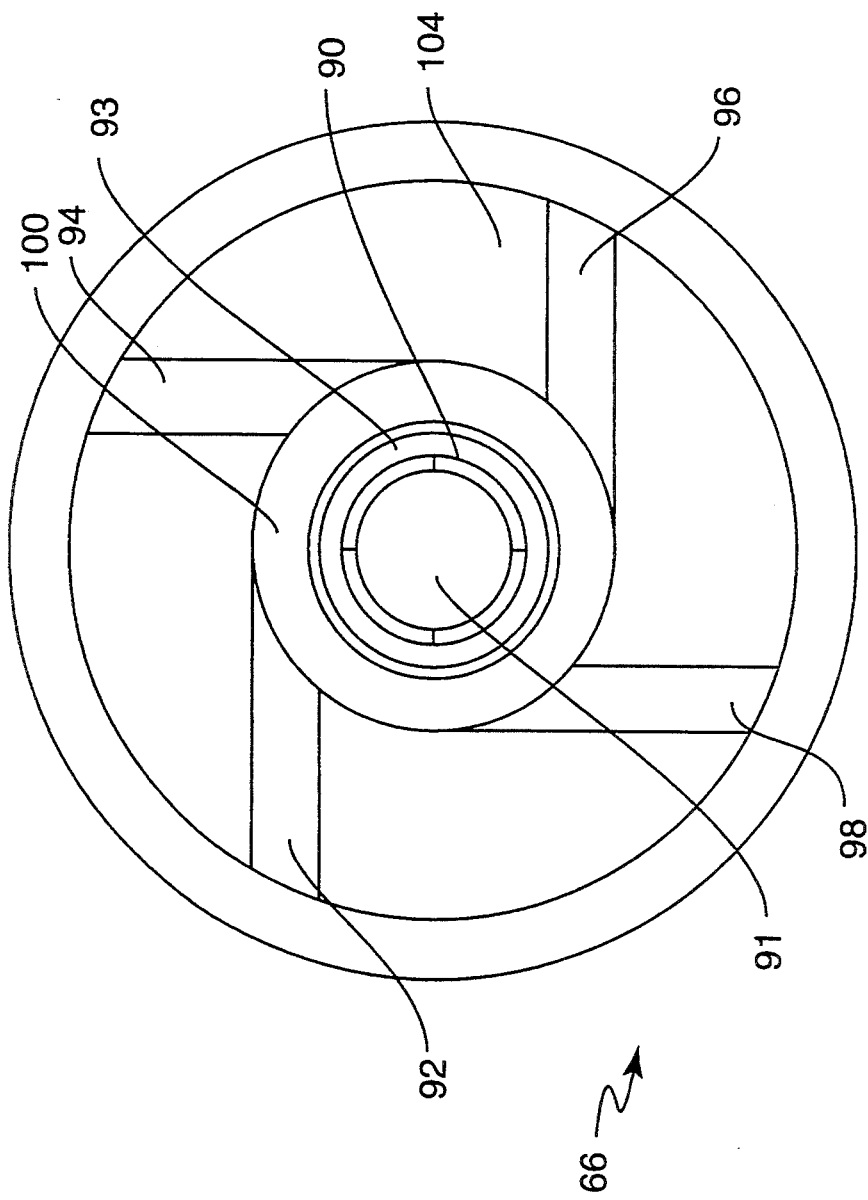
FIG. 9 is a top view of the tip depicted in FIG. 8.

FIGS. 6, 8 AND 9 depict the details of the tip 66, and particularly the shape of the cone 90 and the orientation of the four tangential fluid channels 92, 94, 96, 98. The tip 66 is formed with a disk shaped base 102 having the tapered inlet 91 formed axially therein and into the cone 90. The inner portion of the tip 66 includes the axially extending cone 90 surrounded by the annular parietal channel 100 cut into the disk member 104 extending from the base 102. The tangential fluid channels 92, 94, 96, 98 are cut into the disk member 104 to extend tangentially from the circumference of disk member 104 into the annular parietal channel 100. An annular seat 108 is formed at the periphery of the base 102 at its joinder to the disk shaped member 104 to receive the distal end of the outer sleeve 62. The tangential fluid channels 92, 94, 96, 98 are aligned to match the alignment of the axial channels 82, 84, 86, 88, respectively, when they are aligned in the attachment to the distal end face 75 of inner core 64.

When assembled to the nested sleeve 62 and inner core 64, only the base 102 and inlet 91 are apparent from the outside distal end of the jet probe 60 which is ready to be inserted into blood at a operating site. Of course, a further shield or filter may be provided extending over the distal end of the assembled jet probe to avoid clogging the inlet 91.

After such assembly, and during use, the drive fluid is introduced under pressure into the fluid supply tube 70 and from there into the manifold chamber surrounding the proximal end of the inner core 64. The pressurized drive fluid is forced down the axial fluid channels 82, 84, 86, 88 and into the tangential fluid channels and tangentially into the annular parietal jet channel 100 at the base of the jet nozzle. As mentioned above, the nozzle comprises the outer conical surface 93 of the cone 90 and the tapered inner wall 77 axially aligned to the mixing chamber 76. The vortical flow occurs in the nozzle, exiting at the nozzle plane with the tangential and axial flow components described above. The induced low pressure in inlet 91 lifts the blood into the flow, and the vortex separates entrained air bubbles (and any air induced if the distal end of the jet probe 60 is lifted out of contact with the blood) into the center of the mixing chamber 60, where the air is drawn out through the pipette 80.

Since the parietal fluid jet is designed to be shot into the blood being suctioned, the effect of saline jets on red blood cells is a legitimate concern. Studies have shown that hemolysis can occur at jet velocities of greater than 600 cm/s for a sharp-edged entrance and 1700 cm/s for a well rounded entrance. Other studies have shown a threshold jet velocity of approximately 500 cm/s for sharp-edged entrances. These studies have been considered and the following dimensions are suggested for the sizing of the jet probe 60 and setting operating parameters.

There were five considerations in choosing an appropriate initial design point using one dimensional jet pump theory. First, the design point should be at or near peak efficiency for the chosen flow ratio between suction flow rate and drive flow rate. Second, the "nozzle radius" (the width of the annular gap between cone 90 and wall 77 at the nozzle exit plane) should be greater than 0.0254 cm (a somewhat arbitrary number) for practicality in machining. Third, the drive fluid velocity at the nozzle exit should be below 400 cm/s as a conservative limit to avoid the hemolysis caused by saline jet injection into blood. Fourth, the pressure at the nozzle exit should be low enough to suction blood from the operating site up to the nozzle exit plane (0.5 inch below atmospheric or lower). Finally, the flow ratio should preferably be 0.5 or greater to keep the amount of drive fluid introduced into the bypass or autotransfusion circuit from being excessive.

Addressing these five concerns, the design point at a flow ratio of 0.5 and an area ratio of 0.4 was chosen. The area ratio is the ratio between the jet nozzle annular gap area in the jet nozzle plane and the cross-section area of the mixing chamber. Designing to a nominal suction flow of 400 ml/min., a flow ratio of 0.5 and an area ratio of 0.4 indicates dimensions at the nozzle exit plane for the annular gap of 0.0441 cm wide, the diameter for the mixing chamber 76 of 0.3909 cm, and the inlet diameter within cone 90 of about 0.3028 cm (assuming a line terminus of the frusto conical end of cone 90 at the nozzle exit plane). The mixing chamber is therefore relatively small in diameter, yet the vortical jet action separates the air bubbles centrally in the mixing chamber 76 for evacuation by the pipette 80.

In this design, the lengths of the mixing chamber 76 and the diffuser 78 may be on the order of 1.6 cm and 6.4 cm long, respectively. The exit diameter of diffuser 78 at proximal end 65 may be on the order of 1.06 cm. The inner diameter of the pipette 80 at its tip opening may be 0.1 cm. The primary flow to achieve a suction flow rate of approximately 430 ml/min is 1000 ml/min delivered at an upstream pressure of 56 kPa.

During blood suction with air entrainment, the air removal action of a prototype jet probe configured and operated as described markedly decreased hemolysis levels. Plasma hemoglobin level increases following suction with the prototype are 1.8 ml +/−4.6 mg/dl with air removal and 19.4 +/−8.7 mg/dl without air removal. In side by side comparison with a conventional cardiotomy suction tube, the prototype showed lower levels of hemolysis with air entrainment (−9.1 +/−6.1 mg/dl for the prototype and 5.9 +/−3.6 mg/dl for the conventional tube) and comparable levels of hemolysis without air entrainment than the conventional suction tube. Thus, the vortical jet action is not itself a source of any additional hemolysis.

An additional reduction in red blood cell/air bubble interaction may be accomplished by degassing the drive fluid introduced as the driving jet. The degassed drive fluid quickly absorbs the smallest air bubbles from the blood flow, reducing the chance that any air bubble surface could contact a red blood cell's membrane.

Figure 10:
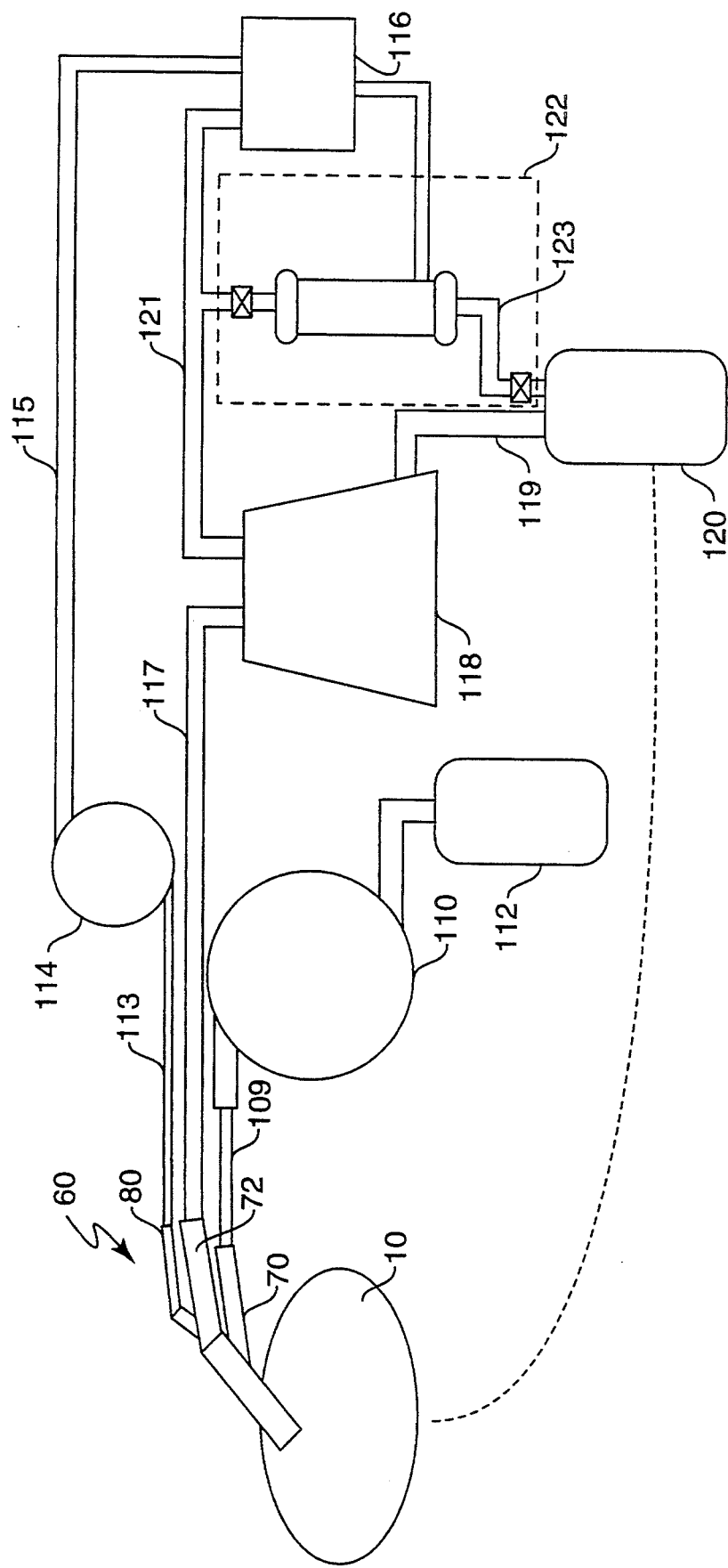
FIG. 10 is a schematic, simplified illustration of an autologous reinfusion system employing the suction probe of FIGS. 4–9 with blood washing prior to reinfusion.

Turning now to FIG. 10, it depicts a blood collection system for autologous transfusion involving the collection of the blood and drive fluid mixture using the jet probe 60 of FIGS. 1–9, and the processing of the recovered red blood cells for reinfusion in the patient. FIG. 10 also depicts an optional plasma processing operation of the type described in the above-referenced '682 patent.

The jet probe 60 is positioned with tip 66 in the patient's operative or postoperative site 10. The fluid supply tube 70 is coupled via a conduit or surgical tubing 109 to a fluid drive pump 110 which pumps drive fluid through a conduit or surgical tubing 111 from a drive fluid source 112. The pipette 80 is coupled by a conduit or surgical tubing 113 to a pump 114 which evacuates the air bubbles in the pipette and pumps the air and fluid through a further conduit or surgical tubing 115 to a waste container 116. The drive fluid and blood mixture is delivered from the exit tube 72 through a conduit or surgical tubing 117 to the blood processing system 118 for further washing and centrifuging to separate the intact red blood cells from plasma, wash and anticoagulant solution and debris using any of the well known processes. The red blood cells are delivered through conduit or surgical tubing to the reinfusion blood bag or container 120, and the remainder is delivered through conduit or surgical tubing 121 to the waste container 116. Optionally, the remainder may be diverted to a plasma processing unit 122 where the plasma may be recovered and delivered through conduit 123 to the reinfusion blood container 120 while the waste is delivered via conduit or surgical tubing 125 to the waste container 116.

During operation, the probe 60 is positioned in the blood in the operative site 10, and drive pump 110 is operated to pump the drive fluid into the annular parietal jet pump where it swirls and exits the jet nozzle into the mixing chamber in the vortex as described above. The vortical action lifts the blood through the tip inlet and mixes it with the drive fluid, entraining the air bubbles in the center of the mixing chamber. The evacuation pump is operated to evacuate the air bubbles through the pipette 80 immediately as they are concentrated by the vortex. The jet action propels the blood and drive fluid mixture to the blood processing system 118 where it is processed as described above.

In a further variation on the use of the jet probe 60 in the system of FIG. 10, it would be possible to employ the probe 60 to irrigate the wound site 10 with drive fluid by substantially reducing the drive flow rate and pressure so that the jet action is halted and the drive fluid is allowed to escape through inlet 91. When irrigation is desired, the pump 114 could be adjusted to a very low pressure or bypassed to allow the drive fluid to provided directly to the manifold 68 and distributed to the tip 66 to escape the inlet 91 as the probe 60 is held with the tip down and moved over the site 10 to effect washing. Then the tip 66 could be immersed in the pooled blood and wash solution and the pump 114 operated as described above to suction it out.

The present invention has been described above in terms of presently preferred embodiments so that an understanding of the present invention can be conveyed in a preferred configuration and use. There are, however, many configurations for suction probes employing jet pump design considerations, and configurations not specifically described herein, but with which the present invention is applicable, may be implemented.

The preferred embodiment depicts the introduction of the primary flow fluid through the four separate jet channels described above to induce the tangential flow. It will be understood that the number of jet channels may be varied.

The preferred embodiment also takes advantage of the capability of evacuating entrained air bubbles immediately after they are suctioned in with blood so as to reduce the probability of blood cell contact leading to lysis and hemolysis. The present invention may find application and provide similar benefits, perhaps to a lesser degree, in other contexts where it is necessary to employ a narrow gauge aspirator tube to access the fluid or material to be suctioned that is too narrow to accommodate the jet pump components described above. In such a context, the narrow gauge aspirator may be coupled to the inlet 91 and extend distally therefrom to the site.

Alternatively, in this regard, the structure of the probe 60 may be implemented in a narrow tubular configuration having a fitting on the tip 66 for connection to such an aspirator, cannula, catheter or surgical tubing for applications proximal to the site.

Moreover, the suction probe of the present invention may be of use in other contexts than the autologous transfusion described above, particularly in other medical uses to aspirate fluids or remove cells where gentle suction is desirable. For example, the jet probe may have applications in collecting and transferring culture or tissue samples. In this regard, a test sample or material may be drawn with a compatible fluid introduced as the drive fluid flow where it is desirable to separate entrained air or lower density, lighter components of the sample or material in the manner described above with respect to blood.

The present invention should therefore not be seen as limited to the particular embodiments described herein, but rather, it should be understood that the present invention has wide applicability with respect to suction probes generally. All modification, variations, or equivalent arrangements that are within the scope of the attached claims therefore should be considered within the scope of the invention.

PARTS LIST FOR FIGURES 1-10 patient's operative or postoperative site 10
reservoir 12
surgical tubing 14
disposable liner bag 16
reusable rigid canister 18
filter 20, 20'
infusion catheter 22
anticoagulant container 24
flexible surgical tubing 26, 28
suction probe or tube 30
surgical tube 38
wash fluid container 40,
reinfusion blood bag 42
reversible pump 44
centrifuge 46
connecting surgical tubes 48, 50, 52, 54
valves 53, 55, 57
section 59
jet pump probe 60
outer tubular sleeve 62
band region 63
inner core 64
proximal end 65
tip 66
plane 67
manifold 68
open end 69
fluid supply tube 70
proximal end 71
blood and drive fluid mixture exit tube 72
annular seat 73
air bubble evacuation tube 74
distal end face 75 mixing chamber 76
conical inner wall 77
conical diffuser 78
pipette 80
open end 81
axial fluid channels 82, 84, 86, 88
hollow jet cone 90
inlet 91
tangential fluid channels 92, 94, 96, 98
cone exterior surface 93
annular channel 100
base 102
disk member 104
annular seat 108
conduit or surgical tubing 109
fluid drive pump 110
conduit or surgical tubing 111
drive fluid source 112
conduit or surgical tubing 113
pump 114
conduit or surgical tubing 115
waste container 116
conduit or surgical tubing 117
blood processing system 118
reinfusion blood bag or container 120
conduit or surgical tubing 121
plasma processing unit 122
conduit 123
conduit or surgical tubing 125

What is claimed is:

1. A suction device for medical purposes for suctioning a material having heavier and lighter components employing a source of pressurized drive fluid, said device comprising:
   an elongated tubular member having a mixing chamber formed therein having a central axis, a tubular side wall and proximal and distal end openings;
   an evacuation tube disposed axially within said mixing chamber aligned with said central axis;
   an inlet formed in communication with said distal end opening for introducing the material to be suctioned into said mixing chamber axially along said center axis; and
   injecting means for injecting said drive fluid into said mixing chamber in a swirling vortex flow around said inlet and said tubular side wall for inducing a suction pressure to draw said material through said inlet into said mixing chamber such that said swirling vortex flow effects the mixture of said heavier components of said material with said drive fluid and the ejection of said mixture through said proximal end opening while concentrating said lighter components axially to be evacuated through said evacuation tube.

2. The device of claim 1 further comprising:
   a diffuser formed in said elongated tubular member proximal to said mixing chamber comprising a frusto conical shaped diffuser chamber having an axis aligned with the axis of said mixing chamber and having a minor diameter end opening aligned with said proximal end opening of said mixing chamber and a major diameter end opening proximal thereto.

3. The device of claim 2 wherein:
   said evacuation tube is disposed axially through said aligned diffuser chamber and said mixing chamber having an evacuation tube opening aligned and spaced proximally from said inlet for evacuating said lighter components as they are concentrated axially by said swirling vortex flow.

4. The device of claim 3 wherein said injecting means further comprises:
   a tip member attached to said distal end opening of said elongated tubular member, said tip member having said inlet formed axially therein extending axially into said mixing chamber and forming a jet pump nozzle with said mixing chamber tubular side wall; and
   means for injecting said pressurized drive fluid tangentially around said inlet in said tip member and said mixing chamber tubular side wall to form a vortex of drive fluid within said jet pump nozzle, whereby said suction device is operable as a parietal jet pump for suctioning in said material through said inlet, mixing said heavier components of said material and said drive fluid in a vortex flow within said mixing chamber and said diffuser chamber, and concentrating said lighter components centrally for evacuation through said evacuation tube.

5. The device of claim 3 wherein said injecting means further comprises:
   a tip member attached to said distal end opening of said elongated tubular member, said tip member having said inlet formed axially therein as a tubular member extending into said distal end opening of said mixing chamber and spaced from said mixing chamber tubular side wall and forming a jet pump nozzle having an annular channel;
   an axial fluid channel extending distally along said elongated tubular member to said tip member;
   a tangential fluid channel formed in said tip member in communication with said annular channel and said axial fluid channel, whereby said drive fluid may be introduced tangentially into said annular channel to swirl around said annular channel and be emitted as a fluid jet in a swirling vortex having a substantial tangential velocity component and a longitudinal velocity component to effect a mixture of said drive fluid with material suctioned into said inlet by said swirling vortex and concentration of lighter components thereof centrally in said mixing chamber for evacuation through said evacuation tube.

6. The device of claim 5 wherein said injecting means further comprises:
   a manifold *formed coaxially about said elongated tubular member in a proximal section thereof providing a manifold chamber for receiving pressurized drive fluid;
   a plurality of said axial fluid channels extending distally from said manifold to said tip member;
   a plurality of said tangential fluid channels formed in said tip member, each tangential fluid channel in communication with said annular channel and one of said axial fluid channels, whereby said drive fluid may be introduced tangentially at a plurality of points around said annular channel.

7. The device of claim 6 wherein said material comprises blood components and other fluids present at an operative site in a patient, said heavier component comprises blood cells, and said lighter component comprises air bubbles.

8. The device of claim 7 wherein said drive fluid comprises a blood compatible wash fluid optionally including a minor proportion of an anticoagulant.

9. The device of claim 1 wherein said material comprises blood components and other fluids present at an operative site in a patient, said heavier component comprises blood cells and plasma, and said lighter component comprises air bubbles.

10. The device of claim 9 wherein said drive fluid comprises a blood compatible wash fluid optionally including a minor proportion of an anticoagulant.

11. The device of claim 1 wherein said materials comprise liquids entrained with a gaseous component and wherein:

said elongated tubular member, said inlet, and said injecting means form an elongated probe body having a distal end adapted to be inserted into said liquid to be collected and having said inlet formed therein, said probe body having a proximal end with a liquid exit formed therein, said mixing chamber centrally disposed within said probe body in communication with said inlet and extending proximally in said probe body, and a diffuser formed within said probe body proximal to said mixing chamber and in communication therewith and with said liquid exit; and said injecting means further comprises a jet pump nozzle formed at said distal end of said probe body in communication with said inlet for receiving said liquids to be collected and directing said liquid into said mixing chamber through suction flow, said jet pump nozzle having a second inlet for receiving said pressurized drive fluid and ejecting said pressurized drive fluid in a swirling vortex around said periphery of said mixing chamber and effecting a sub-atmospheric pressure for suctioning said liquids to be collected and said gaseous component thereof into said inlet, mixing said pressurized drive fluid therewith in said swirling vortex and propelling said mixture into said diffuser while concentrating said gaseous component in the center of said swirling vortex as a stream.

12. The device of claim 11 wherein said material comprises blood components and other fluids present at an operative site in a patient, said heavier component comprises blood cells and plasma, and said lighter component comprises air bubbles.

13. The device of claim 12 wherein said pressurized drive fluid comprises a blood compatible wash fluid optionally including a minor proportion of an anticoagulant.

14. The device of claim 11 wherein said probe body further comprises:

a distribution channel system for channeling said fluid under pressure to said jet pump nozzle; and a gas evacuation tube oriented in relation to said centrally disposed concentrated gaseous component for evacuating said gaseous component from said mixture before said mixture is propelled to said liquid exit.

15. The device of claim 14 wherein said distribution channel system further comprises:

a manifold formed coaxially about said probe body in a proximal section thereof providing a manifold chamber for receiving said pressurized;

a plurality of axial fluid channels extending distally from said manifold to said distal end;

an annular channel formed in said distal end around said inlet and in communication with said mixing chamber;

a plurality of said tangential fluid channels formed in said distal end, each tangential fluid channel in communication with said annular channel and one of said axial fluid channels, whereby said drive fluid may be introduced tangentially at a plurality of points around said annular channel to form said swirling vortex.

16. Apparatus for collection of blood mixed with entrained air bubbles from a patient for reinfusion comprising:

a pressurized source of drive fluid;

a jet pump probe coupled to said pressurized source of drive fluid for drawing blood from a patient including means for mixing said blood and said drive fluid into a mixture in a mixing chamber at a jet pump nozzle exit plane and means for separating said entrained air bubbles from said mixture into a concentrated air bubble stream;

means formed within said jet pump probe for removing said concentrated air bubble stream from contact with said mixture; and a blood collection reservoir having a blood and said drive fluid mixture inlet for receiving said blood and drive fluid from said jet pump probe.

17. The apparatus of claim 16 wherein: said jet pump probe further comprise an elongated body extending between a proximal end, having a drive fluid supply inlet for receiving said drive fluid under pressure and a mixture outlet adapted to be coupled to said blood collection reservoir, and a distal end adapted to be placed in contact with the patient's blood mixed with entrained air bubbles, wherein said distal end of said elongated body is formed with a blood inlet in communication with said jet pump nozzle exit plane, a jet pump nozzle for ejecting said drive fluid in a swirling vortex around a periphery of said mixing chamber effecting a sub-atmospheric pressure for suctioning said blood to be collected and said entrained air bubbles through said blood inlet, and for mixing said drive fluid with said blood into a mixture in said swirling vortex while concentrating said air bubbles in the center of said swirling vortex as a stream; and a distribution channel system extending between said drive fluid supply inlet to said blood inlet for channeling said drive fluid under pressure to said jet pump nozzle; and wherein said removing means further comprises:

an air bubble evacuation tube oriented in said centrally disposed concentrated air bubble stream for evacuating said air bubble stream as said mixture is propelled through said mixing chamber.

18. A probe for use in collecting a liquid entrained with a gaseous component and for separating said gaseous component from the collected liquid employing a pressurized source of drive fluid, said probe comprising:

an elongated probe body having a distal end adapted to be inserted into said liquid to be collected and having a liquid inlet formed therein, said probe body having a proximal end and a liquid exit port formed therein;

a centrally disposed mixing chamber formed in communication with said liquid inlet and having a periphery and extending proximally in said probe body;

a diffuser formed within said probe body proximal to said mixing chamber and in communication therewith and with said liquid exit port;

a jet pump nozzle formed at said distal end in communication with said liquid inlet for receiving and directing said liquid entrained with a gaseous component into said mixing chamber, said jet pump nozzle having a second inlet for receiving said pressurized drive fluid and an ejection port for ejecting said drive fluid in a swirling vortex around said mixing chamber periphery and effecting a sub-atmospheric pressure for suctioning said liquid to be collected and said gaseous component thereof through said liquid inlet, mixing said drive fluid with said liquid into a mixture in said swirling vortex and propelling said mixture into said diffuser while concentrating said gaseous component in the center of said swirling vortex as a stream; and a gaseous component evacuation tube oriented in said centrally disposed concentrated gaseous stream for evacuating said gaseous component stream from said mixture before said mixture is propelled to said liquid exit port.

19. A method of collecting body fluid materials having heavier and lighter components from a patient comprising the steps of:

inserting the distal end of a jet pump probe having a distal suction inlet and a jet pump nozzle exit plane within said jet pump probe into a pool of accumulated body fluid materials;

ejecting pressurized drive fluid into said jet pump nozzle exit plane effecting a sub-atmospheric pressure for suctioning said body fluid materials to be collected into said suction inlet, mixing said heavier components of said body fluid materials and said drive fluid into a mixture in a mixing chamber at said jet pump nozzle exit plane within jet pump probe, and separating said lighter components from said mixture into a concentrated lighter component stream within jet pump probe;

removing said concentrated lighter component stream from contact with said mixture within jet pump probe; and directing said mixture of heavier components and drive fluid from said jet pump probe into a collection reservoir.

20. The method of claim 19, wherein said ejecting step further comprises the steps of:

introducing said drive fluid tangentially into an annular channel surrounding said distal suction inlet to swirl around said annular channel and be emitted as a fluid jet in a swirling vortex having a substantial tangential velocity component and a longitudinal velocity component and kinetic energy to effect said mixture of said drive fluid with said heavier components of said body fluid materials suctioned through said suction inlet and into said mixing chamber at said jet pump nozzle exit plane by said swirling vortex and said separation by concentrating said lighter components centrally in said mixing chamber.

21. The method of claim 20, wherein said directing step further comprises:

channeling said mixture from said mixing chamber into a diffusing chamber within said jet pump probe for converting the kinetic energy of said mixture into pressure energy sufficient to drive said mixture out of said jet pump probe and into said collection reservoir.

22. The method of claim 19 wherein said body fluid materials comprise blood components and other fluids present at an operative site in a patient, said heavier components comprise blood cells and plasma, and said lighter components comprises air bubbles.

23. The method of claim 22 wherein said drive fluid comprises a blood compatible wash fluid optionally including a minor proportion of an anticoagulant.

24. The method of claim 19 wherein said drive fluid comprises a blood compatible wash fluid optionally including a minor proportion of an anticoagulant.

* * * * *